United States Patent [19]
Williams et al.

[11] Patent Number: 5,597,585
[45] Date of Patent: Jan. 28, 1997

[54] VITAMIN/MINERAL COMPOSITION

[76] Inventors: Andrew H. Williams; Eric A. Williams, both of 3608 Heathwood Ct., Jacksonville, Fla. 32277

[21] Appl. No.: 578,284

[22] Filed: Dec. 26, 1995

[51] Int. Cl.$^6$ .......................... A61K 35/28; A61K 35/26; A61K 33/32; A61K 33/24; A61K 31/70; A61K 31/34; A61K 31/355; A61K 31/07
[52] U.S. Cl. .......................... 424/579; 424/580; 424/639; 424/641; 424/655; 514/52; 514/458; 514/474; 514/725
[58] Field of Search .................................. 424/579, 580, 424/639, 641, 655; 514/52, 474, 458, 725

[56] References Cited

U.S. PATENT DOCUMENTS

| 5,198,216 | 3/1993 | McGee | 424/94.2 |
| 5,405,613 | 4/1995 | Rowland | 424/439 |

*Primary Examiner*—Raymond Henley, III
*Attorney, Agent, or Firm*—Arthur G. Yeager; Earl L. Tyner

[57] ABSTRACT

Vitamin/mineral nutritional mixture in the form of a dry powder soluble in water.

4 Claims, No Drawings

5,597,585

VITAMIN/MINERAL COMPOSITION

TECHNICAL FIELD

This invention relates to a novel mixture of vitamins and minerals; and more particularly to such a mixture in the form of a dry powder soluble in water.

BACKGROUND OF THE INVENTION

Vitamins and minerals are universally recognized as components necessary to a healthy body. Generally, it has been the position of the American Medical Association (AMA) that the necessary vitamins and minerals are components of the normal food eaten by people all over the world, and that any supplemental intake of vitamins and/or minerals is unnecessary except in instances of poorly fed people, whether by reason of unavailability of a variety of food stuffs or by reason of a person deliberately refusing to eat well-balanced meals. In any event, there has become available to the public many varieties and recipes for vitamins and minerals to supplement a person's daily intake of food. Generally, these recipes have been compounded into pills such that each pill contains a daily amount of all components in the recipe. There has been developed and issued a listing of all normally used vitamins and minerals with a recommended daily amount for persons in the U.S.A. (known as U.S.R.D.A.). This has become a standard against which other recipes are measured.

It has been generally accepted by AMA that vitamins do not harm the body, if taken in amounts greater than the USRDA amounts, and that any excess vitamins in the body are not accumulated in the body, but are passed through the body waste to the outside. Many persons have declared that excess vitamins in many specific instances are beneficial to the body, and accordingly special recipes have been marketed to serve a variety of purposes, e.g., to relieve stress, to minimize fatigue, to produce extra energy, to induce restfullness, to minimize plaque deposits in the blood stream, to neutralize free radicals in the system, to enhance nerve activity, etc. Linus Pauling, several years ago, led a campaign to partake of large quantities of Vitamin C to function as an oxidizer, which is now understood to mean that Vitamin C neutralized free radicals that otherwise would be detrimental to the health of the individual. Pauling attributed his long life to the use of high doses of Vitamin C. Other research workers have produced other recipes which are alleged to provide other benefits all of which lead to a more healthy body. See, for example, U.S. Pat. No. 5,405,613 to Rowland who suggests a mixture of vitamins, minerals and an esoteric composition from the Far East named "Shilajit", which was a folk remedy for various disorders. U.S. Pat. No. 5,308,627 discloses a nutritional supplement said to treat cellular deficiencies. Other patent disclosures are said to minimize the harmful effects of arteriosclerosis. None of these recipes, however, are designed specifically to be taken as a drink to energize the body with a healthful nutrition.

It is an object of this invention to provide a novel health drink of vitamins and minerals. It is another object of this invention to provide a recipe for vitamins and minerals that includes excess amounts of the components as compared to most compositions available today. Still other objects will appear from the more detailed description which appears below.

BRIEF SUMMARY OF THE INVENTION

This invention relates to a composition of multivitamins and minerals comprising the following components:

| | |
|---|---|
| VITAMIN A | 33,000 TO 40,000 I.U. |
| VITAMIN C | 4,000 TO 5,000 MG. |
| VITAMIN E | 600 TO 650 I.U. |
| VITAMIN B-1 | 20 TO 200 MG. |
| VITAMIN B-2 | 10 TO 50 MG. |
| VITAMIN B-6 | 30 TO 150 MG. |
| VITAMIN B-12 | 30 TO 250 MCG. |
| NIACIN | 40 TO 70 MG. |
| NIACINAMIDE | 20 TO 50 MG. |
| PANTOTHENIC ACID | 20 TO 500 MG. |
| FOLIC ACID | 0.30 TO 0.60 MG. |
| BIOTIN | 30 TO 100 MCG. |
| CHOLINE | 400 TO 725 MG. |
| INOSITOL | 40 TO 100 MG. |
| DL-METHIONINE | 160 TO 1,000 MG. |
| MAGNESIUM | 300 TO 420 MG. |
| POTASSIUM | 100 TO 420 MG. |
| MANGANESE | 5 TO 10 MG. |
| ZINC | 15 TO 30 MG. |
| CHROMIUM | 130 TO 200 MCG. |
| SELENIUM | 200 TO 250 MCG. |
| BETAINE | 120 TO 130 MG. |
| L-CYSTEINE | 660 TO 1,000 MG. |
| THYMUS CONCENTRATE | 30 TO 100 MG. |
| SPLEEN CONCENTRATE | 30 TO 100 MG. |

In a specific and preferred embodiment the composition is best employed in a liquid form; a solution or dispersion of all the components in water. In a special embodiment, the composition is reduced to a dry powder that is sufficient for a daily dose, and is enclosed in a moisture-proof and air-proof package capable of being opened easily and added to water to prepare the previously mentioned liquid.

It is anticipated that certain other components might be added to the above composition, e.g., other vitamins, such as Vitamin D or Vitamin K; or other minerals might be included, e.g., calcium, copper, iron and the like. Furthermore, a preferred additive is ethylenediamine tetraacetic acid (EDTA) or its salts, all of which have a chelation activity; ie., it reacts with metallic ions to remove such ions from the blood stream and thereby eliminates their potential damage to the system These additives are intended to be within the scope of this invention.

DETAILED DESCRIPTION OF THE INVENTION

This invention is centered around the following composition of matter as the critical part of the invention. While other ingredients and components may be added thereto, it is necessary that the following composition be present:

| | |
|---|---|
| VITAMIN A | 33,000 TO 40,000 I.U. |
| VITAMIN C | 4,000 TO 5,000 MG. |
| VITAMIN E | 600 TO 650 I.U. |
| VITAMIN B-1 | 20 TO 200 MG. |
| VITAMIN B-2 | 10 TO 50 MG. |
| VITAMIN B-6 | 30 TO 150 MG. |
| VITAMIN B-12 | 30 TO 250 MCG. |
| NIACIN | 40 TO 70 MG. |
| NIACINAMIDE | 20 TO 50 MG. |
| PANTOTHENIC ACID | 20 TO 500 MG. |
| FOLIC ACID | 0.30 TO 0.60 MG. |
| BIOTIN | 30 TO 100 MCG. |
| CHOLINE | 400 TO 725 MG. |
| INOSITOL | 40 TO 100 MG. |
| DL-METHIONINE | 160 TO 1,000 MG. |
| MAGNESIUM | 300 TO 420 MG. |

-continued

| | |
|---|---|
| POTASSIUM | 100 TO 420 MG. |
| MANGANESE | 5 TO 10 MG. |
| ZINC | 15 TO 30 MG. |
| CHROMIUM | 130 TO 200 MCG. |
| SELENIUM | 200 TO 250 MCG. |
| BETAINE | 120 TO 130 MG. |
| L-CYSTEINE | 660 TO 1,000 MG. |
| THYMUS CONCENTRATE | 30 TO 100 MG. |
| SPLEEN CONCENTRATE | 30 TO 100 MG. |

These components, individually, are not new; but the total composition is new since it represents a nutritional material that has been found to be very beneficial to the maintenance of a healthy, energetic body. The components are separately described below with the U.S. RDA amounts and the biological functions that each component induces. "N/A" means that no amount is recommended in U.S. RDA.

| COMPONENT | U.S. RDA | BIOLOGICAL FUNCTION |
|---|---|---|
| Vitamin A | 5000 IU | Preferably included as Vitamin A acetate Maintenance of healthy skin, eyes, bones, hair and teeth Vitamin A is a powerful antioxidant Vitamin A might help to avoid some types of lung or digestive problems. |
| Vitamin C | 60 MG | Ascorbic Acid - as an antioxidant, inhibits the formation of nitrosamines (a suspected carcinogen) Important for maintenance of bones, teeth, colagen and blood vessels (capillaries) |
| Vitamin E | 30 IU | Preferably included as Vitamin E acetate As an antioxidant, helps protect cell membranes, lipoproteins, fats and Vitamin A from destructive oxidation. Helps protect red blood cells |
| Vitamin B-1 | 1.5 MG | Thiamine hydrochloride - releases energy from foods; needed for normal appetite and for functioning of nervous system |
| Vitamin B-2 | 1.7 MG | Riboflavin-5-phosphate - releases energy from foods; necessary for healthy skin and eyes |
| Vitamin B-6 | 2 MG | Puridoxine - releases energy from foods; plays a role in protein and fat metabolism; essential for function of red blood cells and hemoglobin |
| Vitamin B-12 | 6 MGG | Cyanocobolamine - prevents pernicious anemi necessary for healthy nervous system; involved in synthesis of genetic material (DNA |
| Niacin | 20 MG | Nicotinic Acid - releases energy from foods aids in maintenance of skin, nervous system and proper mental functioning |
| Niacinamide | 20 MG | Same action as Nicotinic Acid but less flushing; lowers cholesterol and improves circulation |
| Pantothenic Acid | 10 MG | Preferably included as calcium salt - releases energy from foods; involved in synthesis of acetylcholine, an excitatory neurotransmitter; needed for normal functioning of the adrenal glands |
| Folic Acid | 400 MCG | Necessary for proper red blood cell formation - plays a role in the metabolism of fats, amino acids, DNA and RNA; needed for proper cell division and protein synthesis |
| VITAMINS | | |
| Biotin | 300 MCG | Releases energy from foods - plays a role in matabolism of amino acids; needed for normal hair production and growth |
| Choline | N/A | Preferably included as choline biartrate As a lipotropic nutrient, prevents fat accumulation in the liver |
| Inositol | N/A | Involved in calcium mobilization |
| DL-Methionine | N/A | Essential amino acid - assists in the breakdown of fats; this amino acid helps the digestive system interact with other substnaces to detoxify harmful agents |
| Magnesium | 400 MG | Preferably included as magnesium oxide - needed in many enzyme systems, especially those involved with energy production; essential for proper heartbeat and nerve transmission; constituent of bones and teeth |
| Potassium | N/A | Preferably included as potassium chloride or citrate - an electrolyte needed to main- |

-continued

| COMPONENT | U.S. RDA | BIOLOGICAL FUNCTION |
|---|---|---|
| | | tain fluid balance, proper heartbeat and nerve transmission |
| Manganese | N/A | Preferably included as manganese oxide - cofactor in many enzyme systems including those involved in bone formation, energy production and protein metabolism |
| Zinc | N/A | Preferably included as zinc gluconate - component of insulin: required in blood sugar control; needed for proper taste and hearing; important in wound healing and enzyme activation |
| Chromium | N/A | Preferably included as chromium proteinate as part of Glucose Tolerance Factor (GTF), it works with insulin to regulate blood sugar levels |
| Selenium | N/A | Preferably included as selenium proteinate as an antioxidant, it is a constituent of glutathione peroxidase; protects Vitamin E |
| Betaine | N/A | Preferably included as betaine hydrochloride digestive enzyme that releases acid in digestive tract |
| AMINO ACIDS | | |
| L-Cysteine | N/A | Preferably included as L-cysteine hydrochloride - has a chelating effect, removing excess copper from the body; free radical destroyer; detoxifies harmful toxins |
| GLANDULARS | | |
| Thymus Concentrate | N/A | Restores healthy immune system function |
| Spleen Concentrate | N/A | Restores low white cell counts - helps fight bacterial infections; possesses immune restorative properties |

It may be seen that among the distinguishing features of this composition are the high (as compared to U.S. RDA) amounts of all vitamins. It is generally believed that excess amounts of vitamin intake to the body is harmless; and this has been verified by use of this invention. Furthermore, it is believed that there are benefits to the body-from the intake of excess amounts of vitamins and accordingly that is a feature of this invention. Each of Vitamins A, C and E is a powerful antioxidant, and the elimination of free radicals in the blood stream and in the body cells is extremely important to the maintenance of good health, since those free radicals are capable of attaching themselves to ionic components and preventing those components from undertaking their natural tasks of cell building, cell repair, purification, attaching infections, and the like.

Still another special benefit from the present composition is the ability to effect chelation, which is a reaction in which an organic radical attaches itself to a different atom or molecule, frequently a metal atom or molecule. The chelation process is very beneficial to the body in that the chelating agent functions similar to an antioxidant in cleansing the system of unwanted materials. Metal atoms can be beneficial in very tiny amounts in the system, but any excess can become toxic and be very debilitating. Thus, atoms of metal may be caught by a chelating agent and flushed out of the body as part of the waste in urine and feces. Chelation also greatly lessens the deposits of plaque and other substances onto the lining of blood vessels. Arteriosclerosis is therefore reduced by the use of the composition of this invention. EDTA is an excellent chelating agent and preferably is included as a component of this composition in amounts of 50 to 100 mg./day. Other body conditions that are benefited by the composition of this invention are heart disease, cholesterol, physiological stress, hypoglycemia, adrenal weakness, arthritis, menopause, candidiasis, premenstrual syndrome, hypertension, osteoporosis, anemia, cataracts, etc.

It should also be noted that three components of the composition; DL-methionine, betaine, and L-cysteine are included in substantial amounts, while the U.S. RDA has no recommendation on the daily amounts of such components for a healthy human. DL-methionine and L-cysteine are both amino acids which are needed in a healthy body along with other amino acids. Betaine is an enzyme, a natural substance that catalyzes body functions. These components function as antioxidants or chelating agents to perform some of the purifying actions mentioned above in the general disclosures and are therefore, very important.

Prior art manufacturers normally compound their vitamin/mineral mixtures into pellets, pills, and the like. However, these compositions are not as stable as could be expected. Oxygen and light cause deterioration of some components, and, therefore, the composition can become stale and lose its effectiveness. Furthermore, a pill does not dissolve in the stomach fluids nearly as quickly as desired. A powder or a solution provides a much more rapid transfer of the vitamins and minerals to the blood stream and to the body cells, completely dissociated into the component parts that can be absorbed by the body cells.

U.S. Pat. No. 4,804,535 suggests that vitamin/mineral compositions need stabilization, and discloses the preparation of an aqueous solution of vitamins/minerals with an unsaturated organic acid to stabilize the mixture. Thus, instability of vitamin/mineral mixtures is well known. This invention prefers to prepare a dry mixture of the vitamin/mineral composition, and seal it in a metal foil pouch so that neither moisture or air can get to the composition until it is ready for use.

The composition preferably is used by mixing the dry component composition in water and drinking the resulting solution. It should be recognized that there may not be a true solution of all components, in that some may only exist as a dispersion in water. Nevertheless, for purposes of this disclosure the word "solution" is intended to include dispersions of dry powder in water, partial solutions and the like, since it is entirely noncritical to the effectiveness of the invention whether the aqueous mixture ingested by the user is a true solution or a partial dispersion.

The composition preferably is in the form of a liquid, a health drink, available to be taken by a human whenever desired. As a drink the chemical and biological constituents of the composition are most quickly infused into the human body; much more quickly than a pellet that is swallowed and must be broken up by the human digestive system before it can be transmitted to the cellular structure to energize and purify the body. It is contemplated by this invention that the composition may be marketed as a bottled health drink or as a water-proof and oxygen-proof package of dry powder. Pellets are considered to be unfavorable, but this invention does include such a physical form.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A composition of multivitamins and minerals comprising the following components in the indicated amounts and optionally including ethylenediamine tetraacetic acid,

| | |
|---|---|
| Vitamin A | 33,000 to 40,000 I.U. |
| Vitamin C | 4,000 to 5,000 mg. |
| Vitamin E | 600 to 650 I.U. |
| Vitamin B-1 | 20 to 200 mg. |
| Vitamin B-2 | 10 to 150 mg. |
| Vitamin B-6 | 30 to 150 mg. |
| Vitamin B-12 | 30 to 250 mg. |
| Niacin | 40 to 70 mg. |
| Niacinamide | 20 to 50 mg. |
| Pantothenic Acid | 20 to 500 mg. |
| Folic Acid | 0.3 to 0.6 mg. |
| Biotin | 30 to 100 mg. |
| Choline | 400 to 725 mg. |
| Inositol | 40 to 100 mg. |
| DL-Methionine | 160 to 1,000 mg. |
| Magnesium | 300 to 420 mg. |
| Potassium | 100 to 420 mg. |
| Manganese | 5 to 10 mg. |
| Zinc | 15 to 30 mg. |
| Chromium | 130 to 200 mg. |
| Selenium | 200 to 250 mg. |
| Betaine | 120 to 130 mg. |
| L-Cysteine | 660 to 1,000 mg. |
| Thymus Concentrate | 30 to 100 mg.; and |
| Spleen concentrate | 30 to 100 mg.. |

2. The composition of claim 1 in the form of a dry powder, soluble in water.

3. The composition of claim 1 in the form of an aqueous solution of said components.

4. The composition of claim 1 wherein ethylenediamine tetraacetic acid is present in an amount of from 50 to 100 mg.

* * * * *